US012595228B2

(12) United States Patent
Queru et al.

(10) Patent No.: US 12,595,228 B2
(45) **Date of Patent: *Apr. 7, 2026**

(54) PROCESS FOR SYNTHESIZING TRIARYLMETHANE SULFONE COMPOUNDS

(71) Applicant: PROVEPHARM LIFE SOLUTIONS, Marseilles (FR)

(72) Inventors: Stephane Queru, Marseilles (FR); Babak Sayah, Marseilles (FR); Nicolas Drillaud, Marseilles (FR); Nicolas Lopez, Marseilles (FR)

(73) Assignee: PROVEPHARM LIFE SOLUTIONS, Marseilles (FR)

( * ) Notice: Subject to any disclaimer, the term of this patent is extended or adjusted under 35 U.S.C. 154(b) by 668 days.

This patent is subject to a terminal disclaimer.

(21) Appl. No.: 17/995,886

(22) PCT Filed: Apr. 1, 2021

(86) PCT No.: PCT/EP2021/058771

§ 371 (c)(1),
(2) Date: Oct. 10, 2022

(87) PCT Pub. No.: WO2021/204711

PCT Pub. Date: Oct. 14, 2021

(65) Prior Publication Data

US 2023/0348372 A1 Nov. 2, 2023

(30) Foreign Application Priority Data

Apr. 10, 2020 (FR) ...................................... 2003638

(51) Int. Cl.

| | |
|---|---|
| ***C07C 213/08*** | (2006.01) |
| ***C07C 303/06*** | (2006.01) |
| ***C07C 303/22*** | (2006.01) |
| ***C07C 315/02*** | (2006.01) |
| ***C07C 315/06*** | (2006.01) |
| ***C09B 11/10*** | (2006.01) |

(52) U.S. Cl.
CPC .......... *C07C 315/02* (2013.01); *C07C 315/06* (2013.01); *C07B 2200/13* (2013.01)

(58) Field of Classification Search
CPC ... C07C 213/08; C07C 303/06; C07C 303/22; C07C 315/02; C07C 315/06; C09B 11/10
See application file for complete search history.

(56) References Cited

U.S. PATENT DOCUMENTS

2019/0010330 A1 1/2019 Vyas et al.

FOREIGN PATENT DOCUMENTS

WO WO 2017/118882 A1 7/2017

OTHER PUBLICATIONS

International Preliminary Report on Patentability issued Nov. 15, 2021, in Corresponding PCT/EP2021/058771, 5 pages.
Bongsup P. Cho et al., "Synthesis and Characterization of N-Demethylated Metabolites of Malachite Green and Leucomalachite Green", Chem. Res. Toxicol. 2003, 16, pp. 285-294.
Yang Guang et al., "Preparation and determination of hydroxybenzene disulfonic acid metal complexes", Fine and Specialty Chemicals, vol. 19, issue (3), 2011, pp. 25-27 (with English Abstract).
International Search Report issued Jun. 9, 2021 in PCT/EP2021/058771 filed on Apr. 1, 2021, 2 pages.
International Preliminary Report on Patentability issued Nov. 15, 2021 in PCT/EP2021/058771 file don Apr. 1, 2021, 5 pages.
Montagut, Ana M. et al., "Triarylmethane Dyes for Artificial Repellent Cotton Fibers", Chem. Eur. J., 2017, vol. 23, total 6 pages.

*Primary Examiner* — Brenda L Coleman
(74) *Attorney, Agent, or Firm* — Oblon, McClelland, Maier & Neustadt, L.L.P.

(57) ABSTRACT

A process for synthesizing a compound of formula (I)

(I)

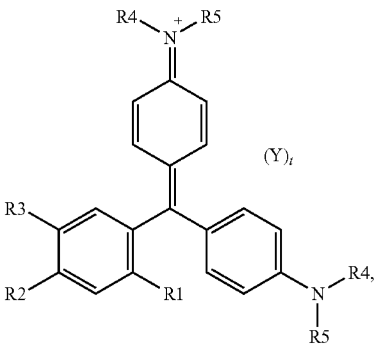

Figure 1:
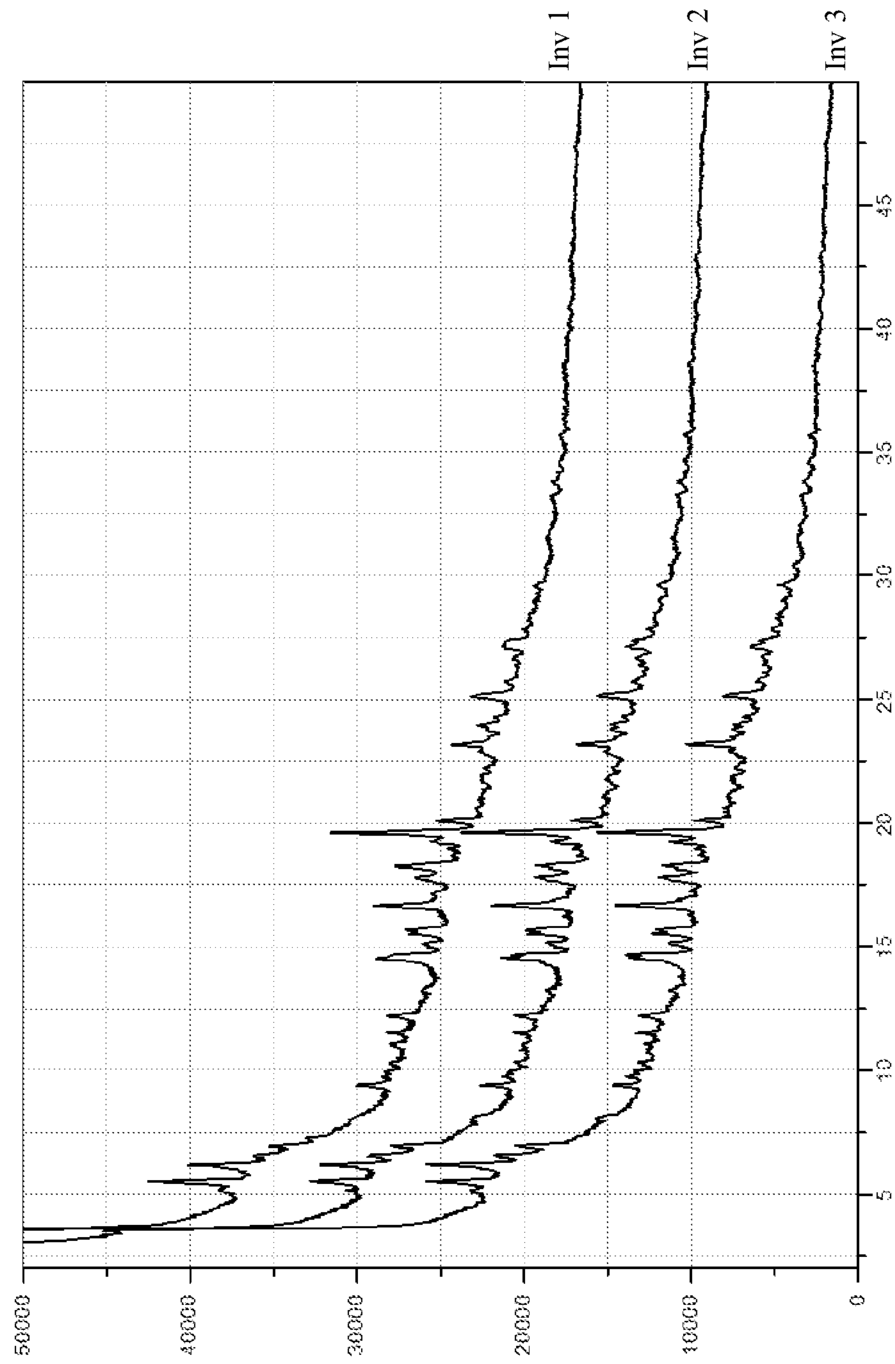

including: (a) condensing the benzaldehyde compound of formula (II) with the dialkylaniline of formula (III) to give the triphenylmethane of formula (IV); (b) treating the triphenylmethane of formula (IV) with sulfuric acid to form the triphenylmethane sulfone of the formula (V); and (c) oxidizing the triphenylmethane sulfone of formula (V) with a quinone. Such a process may be used to prepare patent blue.

15 Claims, 2 Drawing Sheets

PROCESS FOR SYNTHESIZING TRIARYLMETHANE SULFONE COMPOUNDS

CROSS-REFERENCE TO RELATED APPLICATIONS

The present application is the national stage of international application PCT/EP2021/058771, filed on Apr. 1, 2021, and claims the benefit of the filing date of French Appl. No. 2 003 638, filed on Apr. 10, 2020.

TECHNICAL FIELD

The present invention relates to a novel process for synthesizing compounds comprising a triarylmethane structure substituted with sulfone groups, notably a novel process for synthesizing dyes of the family of triarylmethane sulfone compounds, in particular patent blue.

PRIOR ART

Patent blue (4-[[4-(diethylamino)phenyl]-(4-diethylazaniumylidenecyclohexa-2,5-dien-1-ylidene)methyl]-6-hydroxybenzene-1,3-disulfonate salt) is a dye of triarylmethane structure which exists in two forms: the sodium salt [CAS 20262-76-4] and the calcium salt [CAS 3536-49-0]. This dye was first mentioned in 1897 by Ernst Erdmann and Hugo Erdmann, Justus Liebigs Annalen der Chemie, volume 294 (3), 376-392.

In the publications concerning it, there is sometimes confusion between patent blue and isosulfan blue (sodium salt of 2-[[4-(diethylamino)phenyl]-(4-diethylazaniumylidenecyclohexa-2,5-dien-1-ylidene)methyl]benzene-1,4-disulfonate, CAS 68238-36-8 and 748080-29-7), although these molecules are structurally different.

Patent blue is commercially available, but the products that can be found on the market are characterized by a high content of impurities. In particular, there are significant amounts of mono-de-ethylated compound that are difficult to separate from patent blue via conventional purification methods. They are also characterized by a significant amount of residual NaCl.

Patent blue and isosulfan blue are biological tissue dyes that are notably used as contrast agents for lymphatic vessel delineation and are particularly useful as cancer diagnostic agents. They are commonly used in a diagnostic procedure known as “sentinel lymph node mapping”. This method complements lymphography in visualizing the lymphatic system draining the injection area. An important application consists in localizing sentinel lymph nodes in breast cancer patients. Surgical removal of cancerous tissue, guided by patent blue or isosulfan blue, is also performed.

Few authors have focused on the synthesis of patent blue since the 1897 publication by Ernst and Hugo Erdmann. Among these authors, mention may be made of Hagenbach Revue des Colorants Bleus, Helvetica volume 6, issue 1, 1923, pages 134-186; Paul Fritsch, Euric, volume 29, issue 2, May-August 1896, pages 2290-2301. From the basic reactions taught in these documents, a wide variety of dyes can be produced, notably compounds characterized by a triarylmethane sulfone structure.

U.S. Pat. Nos. 1,531,507, 7,534,911, 8,969,616, WO 2017/118 882, WO 2017/218 764 and WO 2018/008 040 report various processes for synthesizing isosulfan blue.

Most of the prior art synthetic methods for manufacturing triarylmethane sulfone dyes include a step of condensation of a sulfonated benzaldehyde with N,N-diethylaniline, this step involving strong acids and resulting in the formation of a leuco base. This step is generally followed by an oxidation step using known oxidizing agents, some of which are known to be hazardous (lead oxide, iron phthalocyanine/oxone), to effect conversion to the triarylmethane dye.

DE 46384 describes a process for synthesizing triarylmethane sulfone dyes, by means of a process involving sulfonation of a triarylmethane structure by treatment with fuming sulfonic acid, followed by oxidation with lead oxide in the presence of sulfuric acid. Neither the product nor its purity is characterized. It is not known what substitutions on the aromatic rings were done. The inventors of the present patent application have found that treatment with fuming sulfonic acid ($SO_3$ gas at saturation in concentrated $H_2SO_4$ solution) degrades the triarylmethane structure very rapidly. The conditions taught by said document thus do not enable the formation of the target structure in satisfactory yields and purity.

The publication A. M. Montagut et al., Chem. Eur. J. 2017, 23, 3810-3814 describes a synthesis of triarylmethane compounds of hydrophobic nature for textile processing. After the formation of the triarylmethane structure substituted with long-chain groups, the last step consists of oxidation with a quinone, 2,3-dichloro-5,6-dicyano-1,4-benzoquinone (DDQ). The corresponding structures are significantly different from conventional dye molecules such as patent blue or isosulfan blue, the aryl nuclei of which are substituted with short-chain groups and which bear sulfone functions.

Among the impurities that are formed during the synthesis of these dialkylaminotriarylmethyl sulfone compounds, the de-alkylated derivatives are particularly interfering. In the case of patent blue and isosulfan blue, impurities are referred to as de-ethylated impurities. Specifically, these molecules differ from the target molecules only by the absence of one or more alkyl (ethyl) groups on the nitrogen atoms. As they are structurally close to the target compounds, they are difficult to remove via conventional purification techniques.

WO 2017/118 882 claims the synthesis of isosulfan blue with a purity >99.8% and an amount of de-ethylated impurity <0.15%. However, the described process involves a step of oxidation with potassium permanganate which leads to manganese contamination. When an attempt is made to apply said method to the synthesis of patent blue, difficulties arise since the raw material, chloro-1-hydroxy-2 benzaldehyde, is not commercially available, and the treatment with sulfonic acid on this molecule does not lead to sulfonation on the appropriate positions.

There was thus still a need for a process for synthesizing triarylmethane sulfone compounds which would make it possible to obtain patent blue but also other derived structures. In particular, it was sought to develop a process that was reproducible, industrially applicable, in good yields, and which yielded products of high purity. In particular, there was still a need for a process that would produce a composition in which the target compound is substantially free of dealkylated derivatives, in particular de-ethylated derivatives in the case of patent blue, but also which does not require the use of heavy metals.

There was also a need for a method for preparing patent blue that would lead to a product that was substantially free of salts.

Surprisingly, the Applicant discovered a process that affords access to compounds of triarylmethane sulfone structure from simple and readily available molecules, in three steps, in high yields and purity. The process of the invention affords access to products that have both satisfactory organic purity and satisfactory purity with respect to metals, while at the same time having good yields.

SUMMARY OF THE INVENTION

The invention relates to a process for synthesizing a compound corresponding to the formula [Chem I]

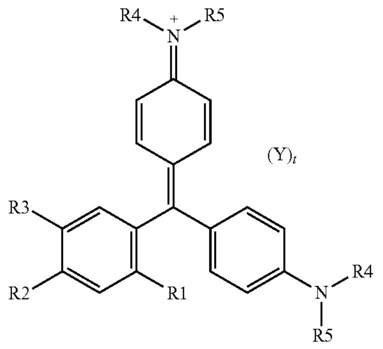

in which

R1 and R2 represent, independently of each other, a group chosen from: —$SO_3H$ and —$SO_3^-$, R3 represents a group chosen from: —OH, —OR', —OCOOR', where R' represents a $C_1$-$C_8$ alkyl, a $C_1$-$C_8$ alkenyl, a phenyl or a benzyl, R4 and R5, which may be identical or different, represent a group chosen from: a $C_1$-$C_8$ alkyl, a $C_1$-$C_8$ alkenyl, a phenyl or a benzyl, it being understood that two groups R4 and R5 borne by the same nitrogen atom may together form a ring including said nitrogen atom, Y represents an organic or inorganic cation chosen from pharmaceutically acceptable salts;

t represents a number, t=0; ½; 1;

this process comprising at least the following steps:

a) condensing the benzaldehyde compound of the formula [Chem II] with the dialkylaniline of the formula [Chem III] to give the triphenylmethane of the formula [Chem IV],

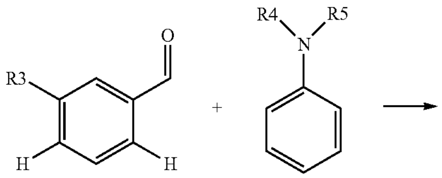

(Chem II) (Chem III)

-continued

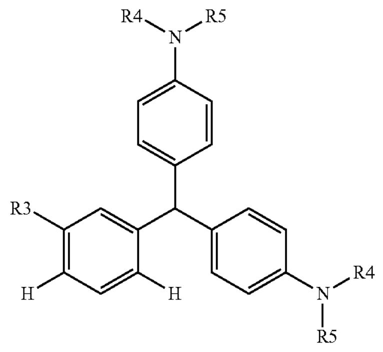

(Chem IV)

b) treating the triphenylmethane of the formula [Chem IV] with sulfuric acid to form the triphenylmethane sulfone of the formula [Chem V],

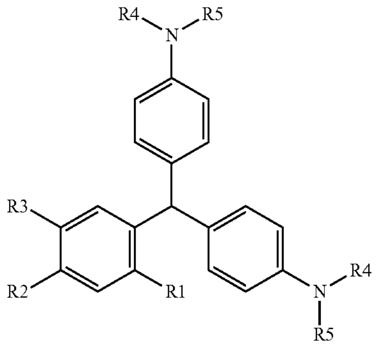

in which R1, R2, R3, R4 and R5 have the same definition as in the formula [Chem I]

c) oxidizing the triphenylmethane sulfone of the formula [Chem V] with a quinone.

According to a preferred embodiment, the process includes, after step c), a salification step d).

According to a preferred embodiment, the compound corresponding to the formula [Chem I] is chosen from those corresponding to the formula [Chem IA]

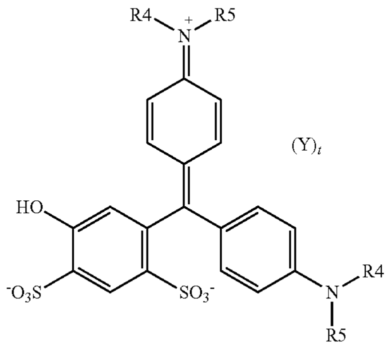

According to a preferred embodiment, the compound corresponding to the formula [Chem IA] is chosen from:

[Chem VI]

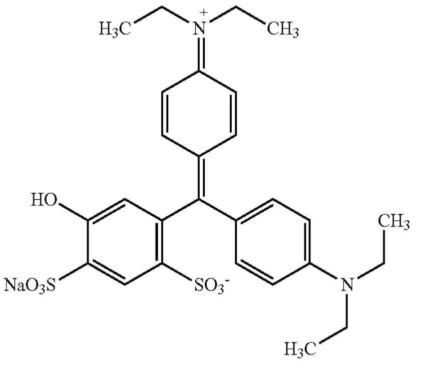

Patent blue, sodium salt

[Chem VII]

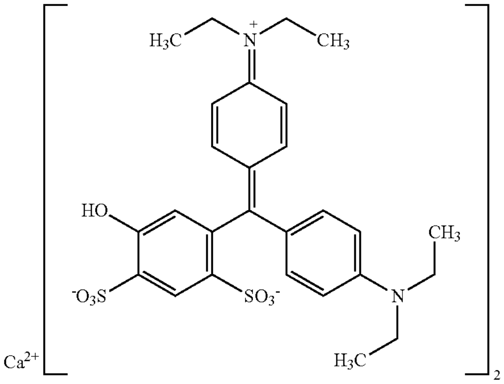

Patent blue, calcium salt

[Chem VIII]

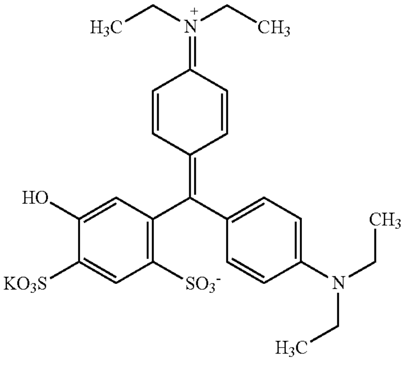

Patent blue, potassium salt

According to a preferred embodiment of the process, in step b), the reaction medium is maintained at a temperature ranging from 70° C. to 120° C. for a period ranging from 1 to 5 hours.

According to a preferred embodiment of the process, on conclusion of step b), the triphenylmethane sulfone of the formula [Chem V] is precipitated out.

According to a preferred embodiment of the process, in step c), the quinone is chosen from 1,4-benzoquinone, 1,2-benzoquinone, a di($C_1$-$C_4$)alkyl-1,4-benzoquinone, a di($C_1$-$C_4$)alkyl-1,2-benzoquinone, a mono($C_1$-$C_4$)alkyl-1,4-benzoquinone and a mono($C_1$-$C_4$)alkyl-1,2-benzoquinone, preferably 1,4-benzoquinone.

According to a preferred embodiment of the process, in step c), the treatment is performed in an apolar protic solvent, at a temperature ranging from 40 to 120° C.

The invention also relates to the use of the process as defined above and as detailed below, for obtaining a composition comprising at least 99.0% of compound corresponding to the formula [Chem I], the percentage being measured by high-performance liquid chromatography with detection at 230 nm.

The invention also relates to the use of the process as defined above and as detailed below, for obtaining a composition comprising at least 99.0% of compound corresponding to the formula [Chem IA], the percentage being measured by high-performance liquid chromatography with detection at 230 nm

[Chem IA]

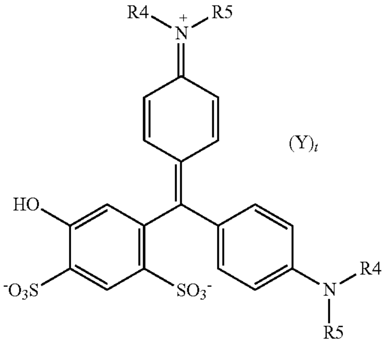

Advantageously, the process is directed towards producing a composition in which no impurity other than a monodealkylated derivative is present in an amount of greater than 0.1%, the percentage being measured by high-performance liquid chromatography with detection at 230 nm.

The invention also relates to the use of the process as defined above and as detailed below, for obtaining a crystalline form of the compound patent blue, sodium salt, corresponding to the formula [Chem VI],

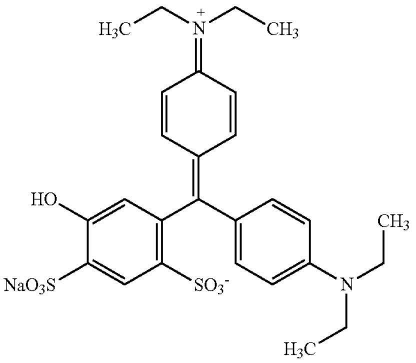

characterized by the following X-ray powder diffraction diagram, measured on a diffractometer and expressed in terms of interplanar spacings d, 2 theta Bragg angle, intensity and relative intensity (expressed as a percentage relative to the most intense line):

| 2 theta angle (°) | Interplanar spacing d (Å) | I (counts) | I rel (%) |
|---|---|---|---|
| 5.6 | 15.80 | 500 | 61.5 |
| 6.2 | 14.29 | 375 | 46.2 |
| 9.4 | 9.39 | 187.5 | 23.1 |
| 10.9 | 8.12 | 62.5 | 7.7 |
| 11.5 | 7.71 | 125 | 15.4 |
| 12.1 | 7.33 | 156.25 | 19.2 |
| 14.4 | 6.14 | 343.75 | 42.3 |
| 15.6 | 5.68 | 250 | 30.8 |
| 16.5 | 5.38 | 375 | 46.2 |
| 17.6 | 5.02 | 187.5 | 23.1 |
| 18.2 | 4.86 | 375 | 46.2 |
| 19.4 | 4.57 | 812.5 | 100.0 |
| 20.0 | 4.43 | 500 | 61.5 |
| 22.9 | 3.87 | 187.5 | 23.1 |
| 24.7 | 3.60 | 250 | 30.8 |

it being understood that the values of the intensity (I) and of the relative intensity (I rel) of the above peaks are liable to vary by +15%.

Advantageously, the crystal structure is substantially free of NaCl, preferably totally free of NaCl.

The invention also relates to a process for manufacturing a medicament or a diagnostic product comprising a) the manufacture of the compound corresponding to the formula [Chem I], preferably patent blue, via the process as described above and as detailed below and b) the introduction of the compound corresponding to the formula [Chem I] into a pharmaceutically acceptable support.

The invention also relates to a composition comprising at least 99.0% of a compound corresponding to the formula [Chem VI] or to the formula [Chem VII], or to the formula [Chem Vill], the percentage being measured by high-performance liquid chromatography with detection at 230 nm:

[Chem VI]

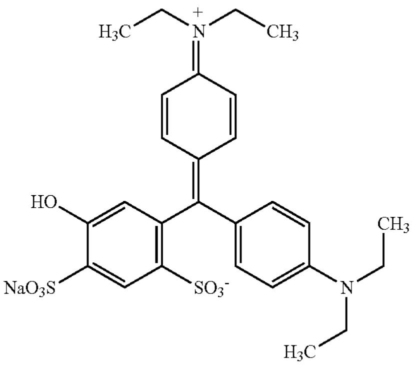

Patent blue, sodium salt

-continued

[Chem VII]

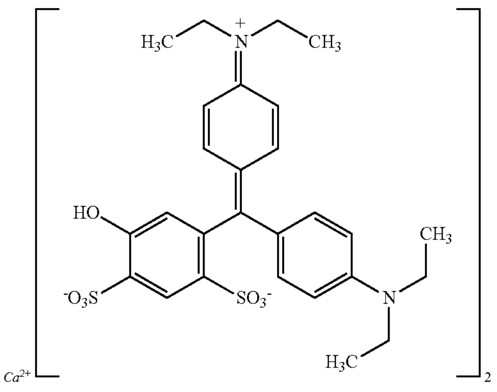

Patent blue, calcium salt

[Chem VIII]

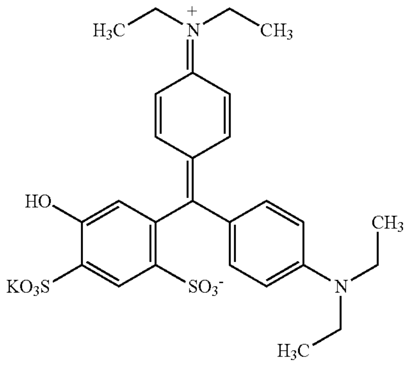

Patent Blue, Potassium Salt

Advantageously, in this composition, no impurity other than a mono-dealkylated derivative is present in an amount of greater than 0.1%, the percentage being measured by high-performance liquid chromatography with detection at 230 nm.

The process of the invention has the advantage of giving access to a composition that is substantially free of NaCl, preferably totally free of residual NaCl.

The invention also relates to a pharmaceutical composition comprising at least one composition comprising a compound of the formula [Chem I], in particular a compound corresponding to the formula [Chem VI] or to the formula [Chem Vil], or to the formula [Chem VIII], as described above and as detailed below, in a pharmaceutically acceptable support. Preferably, it relates to a pharmaceutical composition comprising at least one composition comprising a compound corresponding to the formula [Chem VI] or to the formula [Chem VII].

DETAILED DESCRIPTION

The expression "consists essentially of" followed by one or more features means that, besides the explicitly listed components or steps, components or steps which do not significantly modify the properties and features of the invention may be included in the process or the material of the invention.

The expression "between X and Y" includes the limits, unless explicitly mentioned otherwise. This expression thus means that the targeted range comprises the values X and Y and all the values ranging from X to Y.

Compounds Obtained Via the Process of the Invention

The present invention relates to a process for obtaining compounds corresponding to the formula [Chem I] below:

[Chem I]

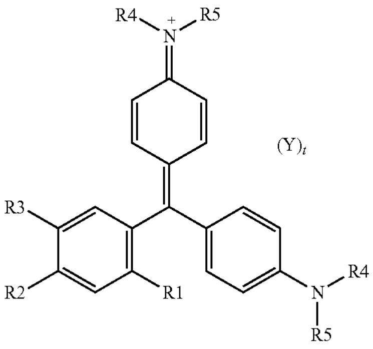

in which

R1 and R2 represent, independently of each other, a group chosen from: —$SO_3H$, —$SO_3^-$, R3 represents a group chosen from: —OH, —OR', —OCOOR', where R' represents a $C_1$-$C_8$ alkyl, a $C_1$-$C_8$ alkenyl, a phenyl or a benzyl, R4 and R5, which may be identical or different, represent a group chosen from: a $C_1$-$C_8$ alkyl, a $C_1$-$C_8$ alkenyl, a phenyl or a benzyl, and two groups R4 and R5 borne by the same nitrogen atom may together form a ring including said nitrogen atom, Y represents an organic or inorganic cation chosen from pharmaceutically acceptable salts;

t represents a number, t=0; ½; 1.

Preferably, in the formula [Chem I]:

R1=—$SO_3H$ or —$SO_3$; R2=—$SO_3H$ or —$SO_3$; R3=—OH.

When two groups R4, R5 borne by the same nitrogen atom together form a ring, these groups can consist of a single alkyl or alkenyl chain, which forms a ring including the nitrogen atom.

Advantageously, R4 and R5, which may be identical or different, represent a group chosen from: a $C_1$-$C_6$ alkyl, a phenyl or a benzyl, and two groups R4 and R5 borne by the same nitrogen atom may together form a chain-(CH2)p-, where p is an integer and p=2 to 5.

Even more advantageously, R4 and R5, which may be identical or different, represent a group chosen from: a $C_1$-$C_3$ alkyl, preferably from methyl and ethyl. Preferably, (R4; R5) is chosen from (CH3; CH3), (C2H5; C2H5) and (CH3; C2H5).

According to a preferred embodiment, R4=R5.

Even more advantageously, (R4; R5) is chosen from (CH3; CH3) and (C2H5; C2H5).

According to a preferred variant, (R4; R5) represents (C2H5; C2H5).

Advantageously, the pharmaceutically acceptable salts denote non-toxic salts in which the cation is chosen from alkali metal ions, alkaline-earth metal ions, or an ammonium ion. Even more advantageously, Y represents a group chosen from: $Na^+$, $Ca2^+$, $K^+$, Mg2+, an ammonium group $NH_4^+$.

More preferably, Y represents a group chosen from: $Na^+$, $Ca^{2+}$.

According to a preferred variant, the process of the invention relates to the production of compounds corresponding to the formula [Chem IA] below:

[Chem IA]

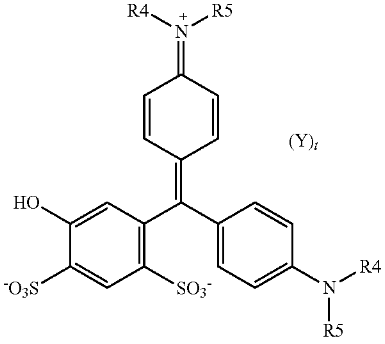

in which R4, R5, Y and t have the same definition as in the formula [Chem I]. The preferences expressed above for the choice of these variables in the context of the formula [Chem I] also apply to the formula [Chem IA].

In particular, the invention relates to the following compounds:

[Chem VI]

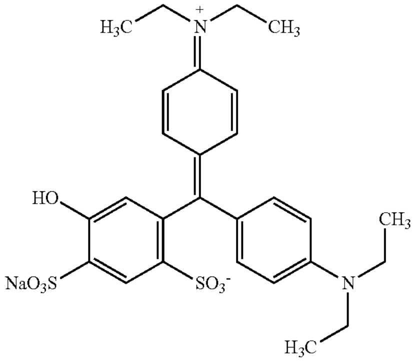

Patent blue, sodium salt

[Chem VII]

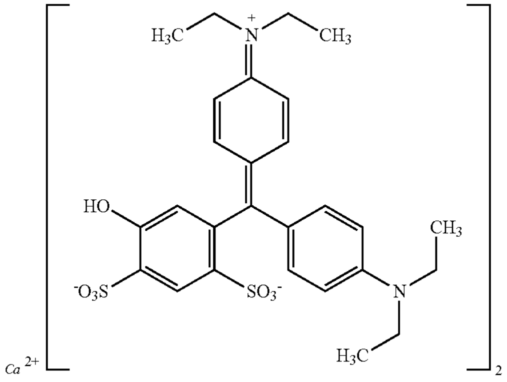

Patent blue, calcium salt

-continued

[Chem VIII]

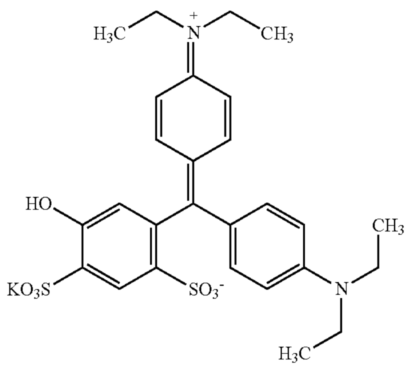

Patent Blue, Potassium Salt

Throughout the patent application, when patent blue is mentioned, it refers to a compound corresponding to the formula [Chem VI] or to the formula [Chem VII] or to the formula [Chem VIII].

Process for Preparing a Compound According to the Invention

The invention relates to a process for synthesizing a compound corresponding to the formula [Chem I], this process comprising at least the following steps:

(a) condensing the benzaldehyde compound of the formula [Chem II] with the dialkylaniline of the formula [Chem III] to give the triphenylmethane of the formula [Chem IV],

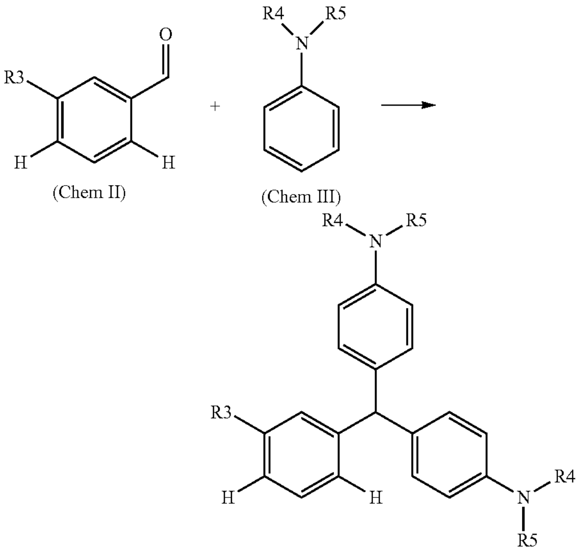

(Chem II) (Chem III)

(Chem IV)

in which

R3 represents a group chosen from: —OH, —OR' and —OCOOR',

R4 and R5 have the same definition as in the formula [Chem I], b) treating the triphenylmethane of the formula [Chem IV] with sulfuric acid to form the triphenylmethane sulfone of the formula [Chem V]

[Chem V]

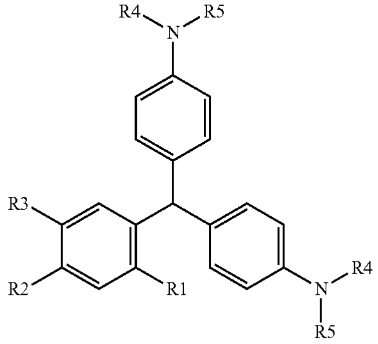

in which R1, R2, R3, R4 and R5 have the same definition as in the formula [Chem I], c) oxidizing the triphenylmethane sulfone of the formula [Chem V] by means of a treatment with a quinone.

The preferences expressed above for the choice of variables R4 and R5 in the context of the formula [Chem I] also apply to the formulae [Chem II], [Chem III], [Chem IV] and [Chem V].

As follows from the schemes above and below, step b) involves the substitution of two hydrogen atoms from among an $SO_3H/SO_3^-$ function.

Step a):

Step a) consists in condensing the benzaldehyde compound of the formula [Chem II] with the dialkylaniline of the formula [Chem III] to give the triphenylmethane of the formula [Chem IV]. Preferably, in the formulae [Chem II] and [Chem IV]:

R3=OH.

Advantageously, in the preparation process defined above, step a) is performed with 1.95 to 3 molar equivalents of dialkylaniline of the formula [Chem III], relative to the amount of benzaldehyde of the formula [Chem II].

Advantageously, in the preparation process defined above, step a) is performed in the presence of urea and in acidic medium. Preferably, the reaction medium is acidified by means of hydrochloric acid. More advantageously, the reaction medium is acidified with 1.2 to 3 molar equivalents of hydrochloric acid relative to the amount of benzaldehyde of the formula [Chem II]. Preferably, step a) is performed in the presence of 0.25 to 1.5 molar equivalents of urea, relative to the amount of benzaldehyde of the formula [Chem II].

Advantageously, in the preparation process defined above, step a) is performed in a solvent chosen from protic solvents, in particular alcohols. Preferably, it is performed in ethanol. Preferably, ethanol is introduced into the reaction medium in an amount ranging from 1 to 6 volumes relative to the mass of the aldehyde of formula [Chem II].

Advantageously, the reaction of step a) is performed by heating at a temperature ranging from 60° C. to 120° C. for 5 to 30 hours, even more advantageously at a temperature ranging from 75° C. to 100° C. for 10 to 25 hours.

Advantageously, on conclusion of the condensation reaction of step a), the reaction medium is treated so as to precipitate the compound of the formula [Chem IV]. Preferably, this precipitation is brought about by the addition to the reaction medium of a solvent chosen from an acidic aqueous solution, acetone, and mixtures thereof.

Advantageously, the compound of the formula [Chem IV] is isolated from the reaction medium by filtration and purified by washing. Advantageously, the washing is performed using a solvent chosen from an acidic aqueous solution, acetone, and mixtures thereof.

Alternatively, it could be envisaged to isolate the compound of the formula [Chem IV] from the reaction medium via other purification techniques such as solvent extraction or chromatography, notably column chromatography on silica.

In the case where the compound [Chem I] is the compound [Chem IA], step a) can be summarized by the scheme below:

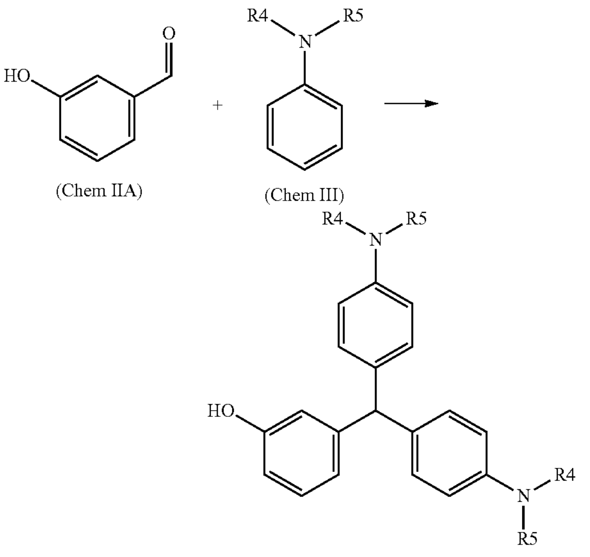

(Chem IIA) (Chem III)

(Chem IVA)

In particular, in the case of the synthesis of patent blue, step a) can be summarized by the scheme below:

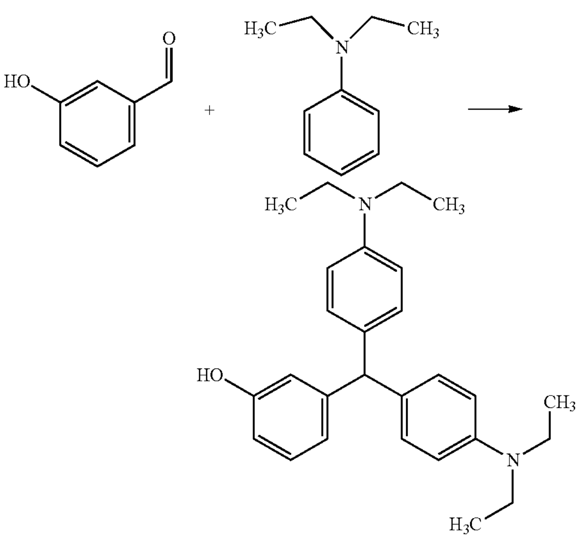

(CHEM IV A - BP)

Step b):

Advantageously, in the preparation process defined above, step b) is performed by means of treatment with concentrated sulfuric acid. For example, use is made of a sulfuric acid solution with a concentration of greater than or equal to 90% by volume, preferably a sulfuric acid solution with a concentration of greater than or equal to 95% by volume.

Preferably, the treatment comprises the addition of the compound of formula [Chem IV] in 1 to 5 volumes of sulfuric acid.

Advantageously, the solution of the compound of formula [Chem IV] in sulfuric acid is heated at a temperature ranging from 60 to 120° C. for a period ranging from 30 min to 10 hours, preferably at a temperature ranging from 80 to 100° C. for a period ranging from 1 hour to 5 hours.

Advantageously, on conclusion of step b), the triphenylmethane sulfone of formula [Chem V] is separated from the reaction medium by precipitation. Preferably, this precipitation is brought about by the addition of a solvent or a mixture of solvents chosen from: alcohols, ethers, water, acetone and mixtures thereof; even more preferentially, by the addition of alcohol (ethanol, isopropanol, etc.), a water/alcohol or water/acetone mixture or an alcohol/ether mixture (isopropanol/isopropyl ether, ethanol/isopropyl ether, etc.).

Alternatively, it could be envisaged to isolate the compound of the formula [Chem V] from the reaction medium via other purification techniques such as solvent extraction or chromatography, notably column chromatography on silica.

Surprisingly, it was found that, under the conditions described above, the sulfonation of the aromatic ring bearing the hydroxyl function in formula [Chem IVa] takes place selectively in the ortho and para positions of the ring when said ring includes a meta-OH group.

In the case where the compound [Chem I] is the compound [Chem IA], step b) can be summarized by the scheme below:

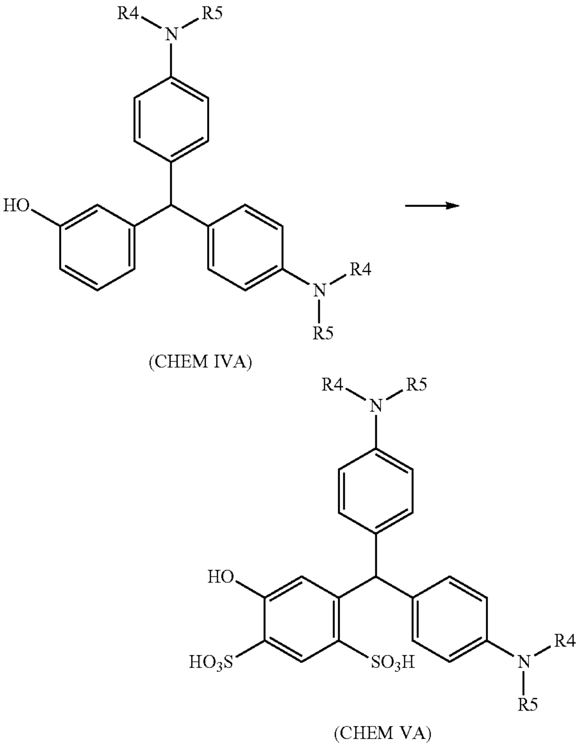

(CHEM IVA)

(CHEM VA)

Step b) is thus particularly advantageous for the synthesis of compounds corresponding to the formula [Chem IA] which has been defined above. In particular, it makes it possible to obtain patent blue with a high selectivity as regards the substitution of the ring bearing the sulfone functions.

Moreover, contrary to what is observed under other sulfonation conditions, the above treatment leads to little formation of by-products due to the degradation of the triarylmethane structure or to the dealkylation of the alkylamine functions.

In the case of patent blue, step b) can be summarized by the scheme below:

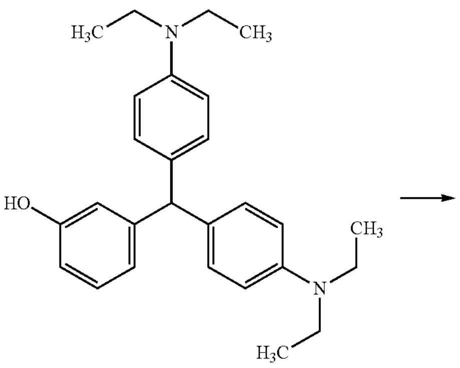

(CHEM IVA-BP)

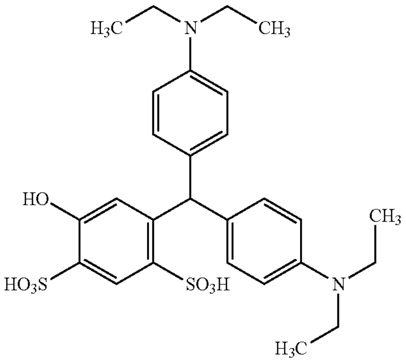

(CHEM VA - BP)

Step c):

In step c), the triphenylmethane sulfone of the formula [Chem V] is oxidized to the target compound of the formula [Chem I] by means of treatment with a quinone. In this step, if the aim is to obtain a high purity product and high conversion yields, it is important to avoid degradation of the triarylmethane structure and dealkylation, i.e. substitution of one or more groups R4, R5 with hydrogen atoms.

The quinone is advantageously chosen from benzoquinones, for instance 1,4-benzoquinone, 1,2-benzoquinone, 3,5-di-tert-butyl-1,2-benzoquinone, 2,5-dimethyl-1,4-benzoquinone, 2-chloro-1,4-benzoquinone and tetrachloro-1,4-benzoquinone.

Preferably, the quinone is chosen from 1,4-benzoquinone, 1,2-benzoquinone, a di($C_1$-$C_4$)alkyl 1,4-benzoquinone, a di($C_1$-$C_4$)alkyl 1,2-benzoquinone, a mono($C_1$-$C_4$)alkyl 1,4-benzoquinone, a mono($C_1$-$C_4$)alkyl 1,2-benzoquinone.

The terms "di($C_1$-$C_4$)alkyl-1,4-benzoquinone" and "di ($C_1$-$C_4$)alkyl-1,2-benzoquinone" mean a quinone bearing two identical or different, preferably identical, $C_1$-$C_4$ alkyl groups, for instance 3,5-di-tert-butyl-1,2-benzoquinone, 2,5-dimethyl-1,4-benzoquinone. The terms "mono($C_1$-$C_4$)alkyl-1,4-benzoquinone" and "mono($C_1$-$C_4$)alkyl-1,2-benzoquinone" mean a quinone bearing a $C_1$-$C_4$ alkyl group, for instance 2-methyl-1,4-benzoquinone.

Preferably the quinone is 1,4-benzoquinone.

Surprisingly, these quinones were found to give a high degree of conversion and low degradation to dealkylated impurities, particularly to de-ethylated impurities in the case of patent blue.

Preferably, in step c), the treatment is performed in an apolar protic solvent. For example, the solvent may be chosen from dimethyl sulfoxide (DMSO), N-methylpyrrolidone (NMP) and dimethylformamide (DMF).

Preferably, in step c), the treatment is performed at a temperature ranging from 40 to 130° C., advantageously at a temperature ranging from 60 to 120° C., even more advantageously from 70 to 110° C.

Advantageously, on conclusion of step c), the target compound of the formula [Chem I] is separated from the reaction medium by precipitation. Preferably, this precipitation is brought about by the addition of a solvent or a mixture of solvents chosen from: alcohols, ethers, water, acetone and mixtures thereof.

Alternatively, it could be envisaged to isolate the compound of the formula [Chem I] from the reaction medium via other purification techniques such as solvent extraction or chromatography, notably column chromatography on silica.

Step d):

When t is other than 0, the process includes, after step c), a salification step d). In a well-known manner, this step is performed by introducing the target compound of the formula [Chem I] obtained from step c) (t=0) into a solvent with the chosen counterion.

In the particular case of patent blue, the counterion is advantageously chosen from $Na^+$, $Ca^{2+}$ and $K^+$, even more preferentially from $Na^+$ and $Ca^{2+}$. However, derivatives of patent blue having another counterion Y, corresponding to the target compound of the formula [Chem IA], may be obtained via the process of the invention.

Optionally, the process may be followed by one or more conventional purification steps such as precipitation, crystallization, solvent extraction or chromatography.

In the case of the compound [Chem IA], steps c) and d) may be summarized by the scheme below:

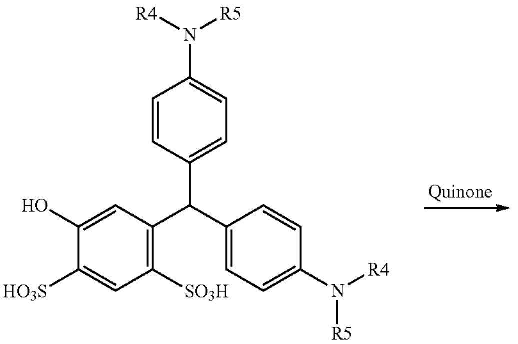

(CHEM VA)

-continued

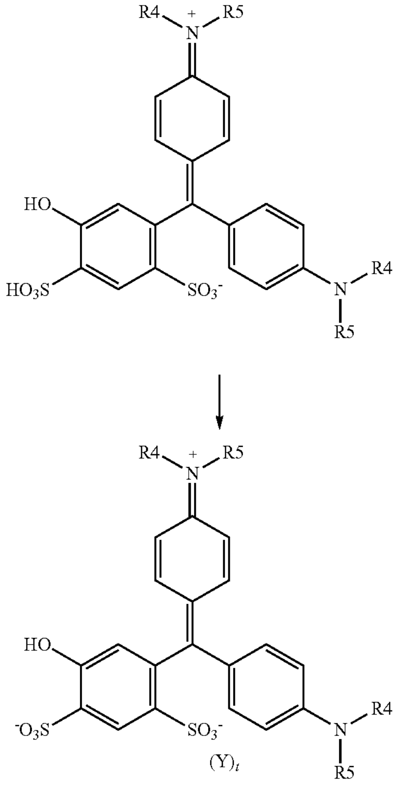

(CHEM IA)

In the case of patent blue (sodium salt), the combination of steps c) and d) may be summarized by the scheme below:

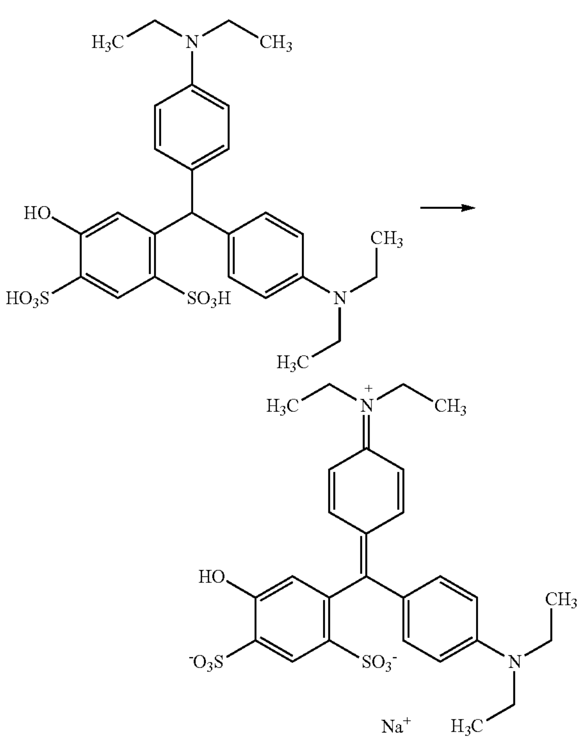

Surprisingly, it was found that the combination of the above two steps affords direct access to a crystalline form of patent blue, in particular of patent blue sodium salt, which was not known in the prior art. The direct production of a crystalline form offers many advantages in terms of yield and purity, but also in terms of efficiency and economy for an application of the process on an industrial scale. The product obtained has crystalline characteristics that give it good stability. The process of the invention offers greater ease of processing insofar as it leads, in a reproducible manner, to a crystalline product, of unique polymorphism, which is necessary in the majority of galenical formulas (in particular dry formulas). The absence of NaCl promotes the solubility of patent blue in aqueous solution.

Characteristics of the Compounds Obtained

The process of the invention affords access to compositions comprising the target compound of formula [Chem I], in particular the compounds [Chem IA] and [Chem IB], more particularly the compounds of formulae [Chem VI], [Chem VII] and [Chem VIII], in high yields and with a very low level of impurities.

In practice, the mono-dealkylated impurity (only one alkyl function among the groups R4 and R5 is replaced with a hydrogen atom, the other three are alkyls) is the main impurity observed during the synthesis of the compounds of formula [Chem I]. Since the other dealkylated impurities are of more remote structure, they have different properties and, if they are formed, they are eliminated during the process.

In particular, the process of the invention affords access to a composition comprising at least 98.0% of compound corresponding to the formula [Chem I], and less than 1% of mono-dealkylated impurity (compound of formula [Chem I] in which one of the groups R4 and R5 represents H), the percentage being measured by high-performance liquid chromatography with detection at 230 nm.

Even more preferentially, the process of the invention affords access to a composition comprising at least 99.0% of compound corresponding to the formula [Chem I], and less than 0.5% of mono-dealkylated impurity, no other impurity being present in an amount of greater than 0.15%.

In particular, the process of the invention affords access to a composition comprising at least 98.0% of compound corresponding to the formula [Chem IA] and less than 1% of mono-dealkylated impurity (compound in which one of the groups R4, R5 represents H), the percentage being measured by high-performance liquid chromatography with detection at 230 nm. Even more preferentially, the process of the invention affords access to a composition comprising at least 99.0% of compound corresponding to the formula [Chem IA], and less than 0.5% of mono-dealkylated impurity, no other impurity being present in an amount of greater than 0.15%.

Advantageously, the process affords access to a composition in which no impurity other than a mono-dealkylated derivative is present in an amount of greater than 0.1%, the percentage being measured by high-performance liquid chromatography with detection at 230 nm.

In the case of patent blue, the de-ethylated impurities are represented by the formulae below in which Y and t have the same definition as above (in particular, $Y=Na^+$ and t=1; $Y=Ca^{2+}$ and t=½):

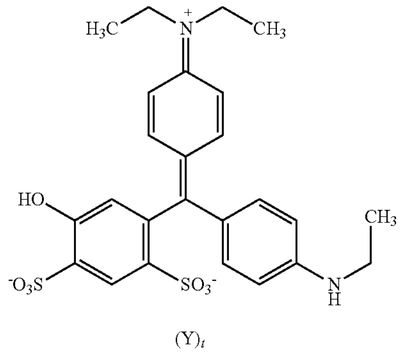

mono-de-ethylated impurity

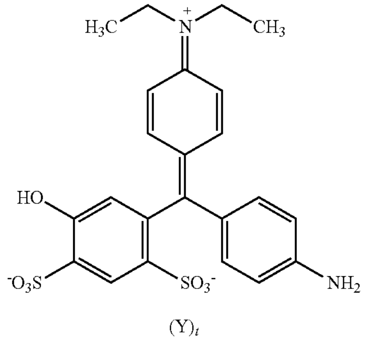

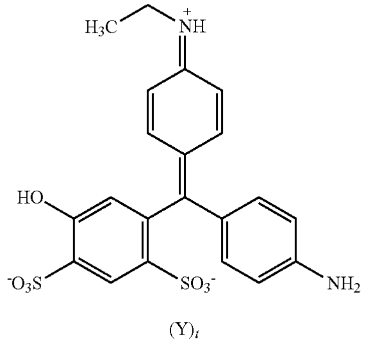

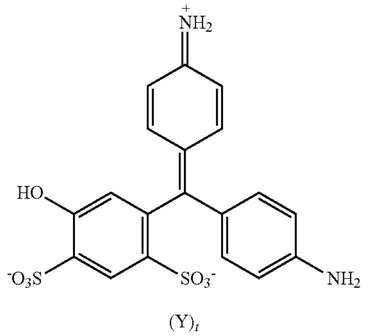

In practice, the mono-de-ethylated impurity (a single ethyl function replaced with a hydrogen atom) is the main impurity observed in the synthesis of patent blue. Since the other de-ethylated impurities are of more remote structure, they have different properties and, if they are formed, they are eliminated during the process.

In particular, the process of the invention affords access to a composition comprising at least 98.0% of 4-[[4-(diethylamino)phenyl]-(4-diethylazaniumylidenecyclohexa-2,5-dien-1-ylidene)methyl]-6-hydroxybenzene-1,3-disulfonate salt (patent blue), and less than 1% of mono-de-ethylated impurity, the percentage being measured by high-performance liquid chromatography with detection at 230 nm.

Even more preferentially, the process of the invention affords access to a composition comprising at least 99.0% of 4-[[4-(diethylamino)phenyl]-(4-diethylazaniumylidenecyclohexa-2,5-dien-1-ylidene)methyl]-6-hydroxybenzene-1,3-disulfonate salt, and less than 0.5% of mono-de-ethylated impurity, no other impurities being present in an amount of greater than 0.15%, the percentage being measured by high-performance liquid chromatography with detection at 230 nm.

Advantageously, the process affords access to a composition in which no impurities other than the mono-de-ethylated derivative are present in an amount of greater than 0.1%, the percentage being measured by high-performance liquid chromatography with detection at 230 nm.

In particular, the process of the invention affords access to a composition comprising at least 98.0% of the sodium salt of 2-[[4-(diethylamino)phenyl]-(4-diethylazaniumylidenecyclohexa-2,5-dien-1-ylidene)methyl]benzene-1,4-disulfonate (isosulfan blue), and less than 1% of mono-de-ethylated impurity, the percentage being measured by high-performance liquid chromatography with detection at 230 nm.

Even more preferentially, the process of the invention affords access to a composition comprising at least 99.0% of N-[4-[[4-(diethylamino)phenyl(2,5-disulfophenyl)methylene]-2,5-cyclohexadien-l-ylidene]-N-ethylethanaminium sodium salt, and less than 0.5% of mono-de-ethylated impurity, the percentage being measured by high-performance liquid chromatography with detection at 230 nm.

Advantageously, the process of the invention affords access to a composition in which no impurities other than the mono-de-ethylated derivative are present in an amount of greater than 0.1%, the percentage being measured by high-performance liquid chromatography with detection at 230 nm.

The process of the invention also affords access to compositions comprising a compound corresponding to the formula [Chem I], in particular the compounds [Chem IA], more particularly the compounds of formulae [Chem VI], [Chem VII] and [Chem VIII], including few or no metal impurities. It goes without saying that the alkali metal and alkaline-earth metal salts which may correspond to Y are not considered to be metal impurities within the meaning of the invention.

The process of the invention notably affords access to compositions comprising a compound corresponding to the formula [Chem I], in particular the compounds [Chem IA], more particularly the compounds of formulae [Chem VI], [Chem VII] and [Chem VIII] and including less than 200 ppm of metal contaminants, advantageously less than 100 ppm of metal contaminants, better still less than 50 ppm of metal contaminants, and even more advantageously less than 20 ppm of metal contaminants.

The content of metal contaminants denotes the content of metals, measured according to the ICP/MS (Inductively Coupled Plasma Mass Spectrometry) method.

The term "metal contaminants" means all the metals of the Periodic Table of Elements, excluding alkali metals and alkaline-earth metals and also the organic and inorganic derivatives thereof. More particularly, the term "metallic contaminants" means "heavy" metals and in particular: Al, As, Cd, Cr, Cu, Fe, Sn, Mn, Hg, Mo, Ni, Pb, Zn and the organic and inorganic derivatives thereof.

The process of the invention also affords access to a crystalline form of the patent blue sodium salt of formula [Chem VI], characterized by the following X-ray powder diffraction diagram, measured on a diffractometer (copper anode) and expressed in terms of interplanar spacings d, 2 theta Bragg angle, intensity and relative intensity (expressed as a percentage relative to the most intense line):

| 2 theta angle (°) | Interplanar spacing d (Å) | I (counts) | I rel (%) |
|---|---|---|---|
| 5.6 | 15.80 | 500 | 61.5 |
| 6.2 | 14.29 | 375 | 46.2 |
| 9.4 | 9.39 | 187.5 | 23.1 |
| 10.9 | 8.12 | 62.5 | 7.7 |
| 11.5 | 7.71 | 125 | 15.4 |
| 12.1 | 7.33 | 156.25 | 19.2 |
| 14.4 | 6.14 | 343.75 | 42.3 |
| 15.6 | 5.68 | 250 | 30.8 |
| 16.5 | 5.38 | 375 | 46.2 |
| 17.6 | 5.02 | 187.5 | 23.1 |
| 18.2 | 4.86 | 375 | 46.2 |
| 19.4 | 4.57 | 812.5 | 100.0 |
| 20.0 | 4.43 | 500 | 61.5 |
| 22.9 | 3.87 | 187.5 | 23.1 |
| 24.7 | 3.60 | 250 | 30.8 |

It should be understood that the values of the intensity (I) and relative intensity (I rel) of the above peaks are liable to vary by ±15%.

In the above table, all the lines are assumed to be first-order (n=1 in Bragg's law).

Medicament:

The invention also relates to a process for manufacturing a medicament or a diagnostic product, comprising the manufacture of the compound corresponding to the formula [Chem I], in particular the compounds [Chem IA], more particularly the compounds of formulae [Chem VI], [Chem VII] and [Chem VIII], preferably patent blue, sodium salt, via the process described above, and the introduction of the compound corresponding to the formula [Chem I] into a pharmaceutically acceptable support.

Said medicament may be in any form that is suitable for use in the intended applications.

In particular, mention may be made of: in the form of a tablet or gel capsule comprising from 1 to 500 mg of compound corresponding to the formula [Chem I]; in the form of an aqueous solution comprising the compound corresponding to the formula [Chem I], preferably patent blue, in particular patent blue, sodium salt, at a concentration ranging from 0.05% to 2% in g/L. Notably, a preferred formulation consists of an injectable aqueous solution.

Such compositions comprise, in addition to the compound of formula [Chem I], excipients that are well known to those skilled in the art, for instance citric acid and/or citrates, a phosphate buffer, polymers, cellulose derivatives or lipids.

In medical applications, the compound of the formula [Chem I], preferably patent blue, when it is obtained via the process of the invention, has the advantage of having high purity, which avoids the introduction into the body of materials that are not useful for the application.

The efficiency of the process of the invention affords access to a product of high purity with reduced costs, in accordance with a method which is readily reproducible and applicable on an industrial scale.

In addition, the process of the invention affords access to a product with a crystalline structure, which thus has good stability.

Such a composition is particularly advantageous for use as a contrast agent for detecting lymphatic vessels and arterial territories and as a cancer diagnostic agent. In particular, the composition of the invention may be used in a diagnostic procedure known as "sentinel lymph node mapping". This procedure most particularly relates to breast cancer, colon cancer and melanoma.

In particular, the composition is particularly advantageous for sentinel lymph node mapping prior to biopsy in patients with operable breast cancer and in intraoperative sentinel lymph node mapping in patients with colon cancer. It is also used in preoperative lymphoscintigraphy for sentinel lymph node biopsy of melanoma.

The various embodiments, variants, preferences and advantages described above for each of the subjects of the invention apply to all the subjects of the invention and may be taken separately or in combination.

The invention is illustrated by the examples that follow, which are given without any implied limitation.

FIGURES

FIG. 1 is a graph representing the X-ray diffraction diagrams of three samples of patent blue, sodium salt, obtained according to the process of the invention (designated Inv1, Inv2 and Inv3). These are samples from three different production batches. On the x-axis: the 2 theta angle in degrees; on the y-axis: the intensity in arbitrary intensity units.

Figure 2:
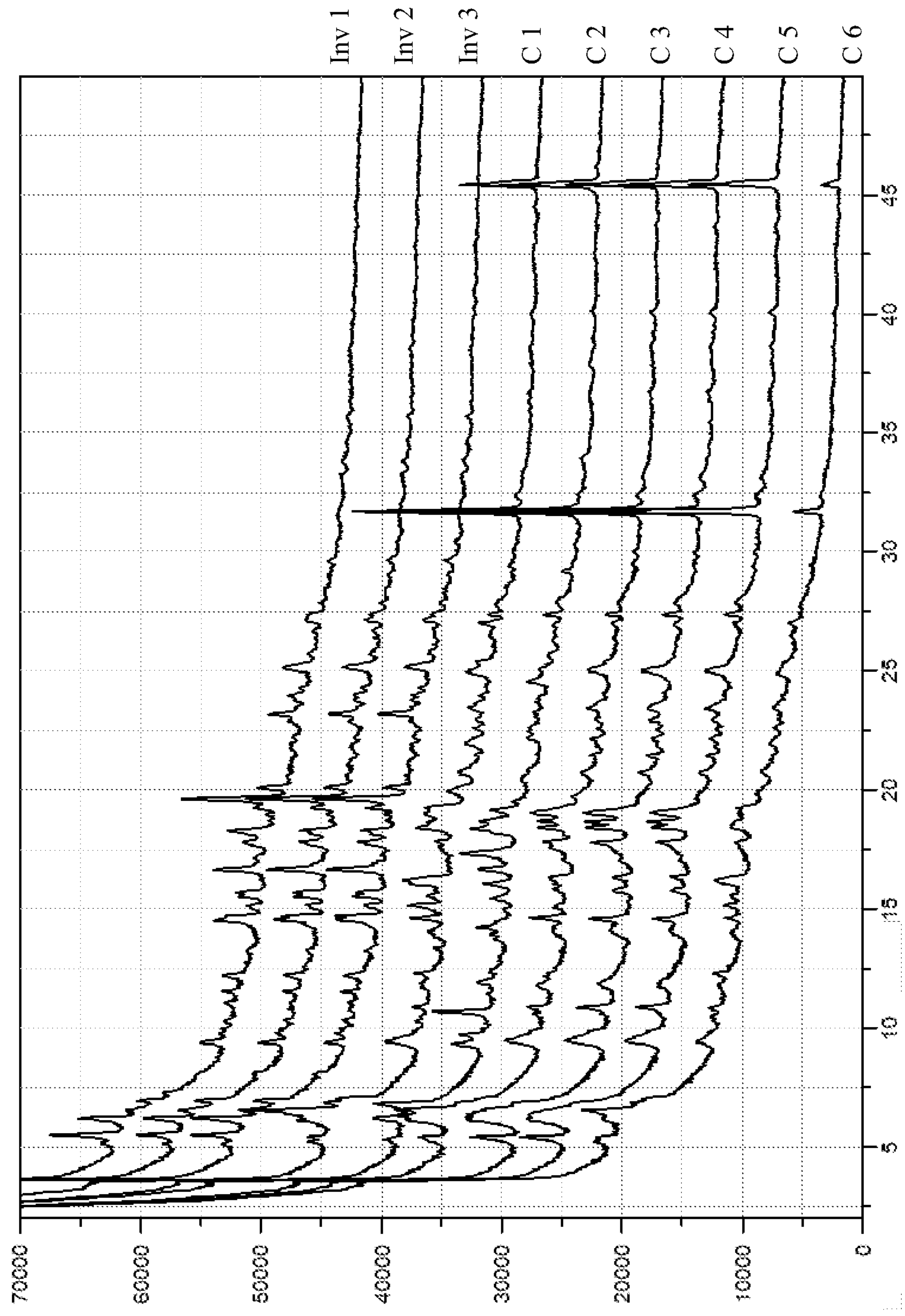

FIG. 2 is a graph representing the X-ray diffraction diagrams of six commercially available samples of patent blue, sodium salt (designated C1 to C6). Also plotted on this figure are the X-ray diffraction diagrams of three samples of patent blue, sodium salt, obtained according to the process of the invention (designated Inv1 to Inv3) and shown in FIG. 1. On the x-axis: the 2 theta angle in degrees; on the y-axis: the intensity in arbitrary intensity units.

EXAMPLES

In these Examples, the parts and percentages are expressed on a weight basis, unless otherwise indicated.

Materials and Methods

HPLC Analysis:

- Column: Agilent Poroshell 120 SB—C18 150×4.6-2.7μ (ref. 683975-902)
- Mobile phase A: 10 mM ammonium formate/formic acid buffer (pH=4.1±0.1)
- Mobile phase B: Acetonitrile
- Flow rate: 1 ml/mn
- Temperature: 30° C.
- Injection volume: 5 μL
- Gradient: Analysis time 40 min+7 min post-run stabilization

TABLE 1

| Time | A % | B % |
|---|---|---|
| 0.0 | 90 | 10 |
| 4.0 | 90 | 10 |
| 12 | 85 | 15 |
| 30 | 10 | 90 |
| 40.0 | 10 | 90 |

TABLE 1-continued

| Time | A % | B % |
|---|---|---|
| 40.1 | 90 | 10 |
| 47.0 | 90 | 10 |

Detector: UV-Vis 230 nm and MS Electrospray (negative mode)

X-ray powder diffractogram: The X-ray powder diffraction diagram was produced under the following experimental conditions:

X'Pert Pro MPD Panalytical diffractometer (DY2764),

Copper anode ($\lambda$=1.54 Å), voltage: 40 kV, current 40 mA

Mounting θ-θ

Measuring range: 2° to 50°

Increment between each measurement: 0.026°

Measurement time per step: 20.40 s,

PIXcel RIMS detector (PHD 25.5-7%, active length 3.347°

Synthesis of Patent Blue

Step 1: Preparation of 3-(bis(4-(diethylamino)phenyl)methyl)phenol dihydrochloride

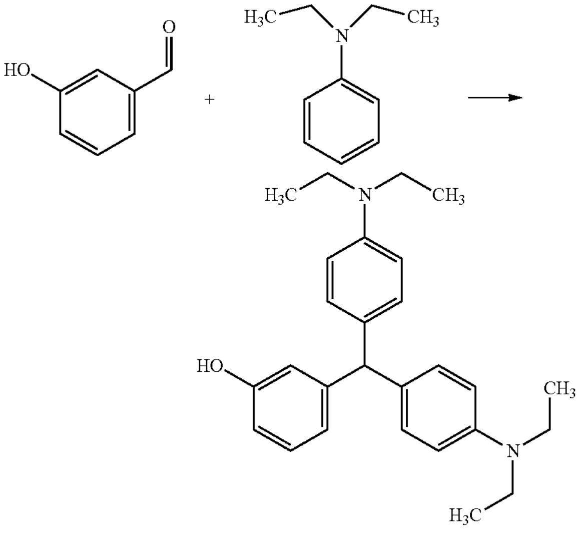

Add N,N-diethylaniline (254.0 mL, 1.597 mol, 1.95 eq) to a mixture of 3-hydroxybenzaldehyde (100 g, 0.819 mol, 1.00 eq) and urea (24.6 g, 0.409 mol, 0.50 eq) in 100 ml of ethanol.

Cool the reaction medium to 0° C. and pour in aqueous 37% HCl solution (136.5 mL, 1.638 mol, 2.00 eq), while keeping the medium at a temperature below 20° C.

Next, reflux the reaction medium for 20 hours.

Cool the reaction medium to 60° C. and then pour in 800 mL of aqueous 2N HCl solution.

Cool the reaction medium to 0° C. and continue stirring for 5 hours.

Filter off the precipitate obtained and wash the solid with 500 ml of a 2N aqueous acetone/HCl mixture (9/1) and then 500 ml of acetone.

The solid is dried in a ventilated oven (50° C.).

303 g of 3-(bis(4-(diethylamino)phenyl) methyl) phenol dihydrochloride are obtained in the form of a white solid.

HPLC purity: 97.2%

Yield: 78%

$^{1}$H NMR (300 MHz, D2O): δ 7.39 (4H, dd, J=8.7 Hz), 7.33 (4H, dd, J=8.7 Hz), 7.22 (1H, t, J=7.9 Hz), 6.80 (1H, ddd), 6.71 (1H, dd, J=7.8 Hz), 6.67 (1H, t, J=2.0 Hz), 5.67 (1H, s), 3.60 (8H, q, J=6.9 Hz), 1.06 (12H, t, J=7.2 Hz)

$^{13}$C NMR (75 MHz, D2O): δ 156.0, 145.5, 144.3, 135.1, 131.2, 130.3, 122.4, 121.4, 116.2, 114.0, 54.9, 53.7, 9.7

Step 2: Preparation of 4-(bis(4-(diethylamino)phenyl) methyl)-6-hydroxybenzene-1,3-disulfonic acid

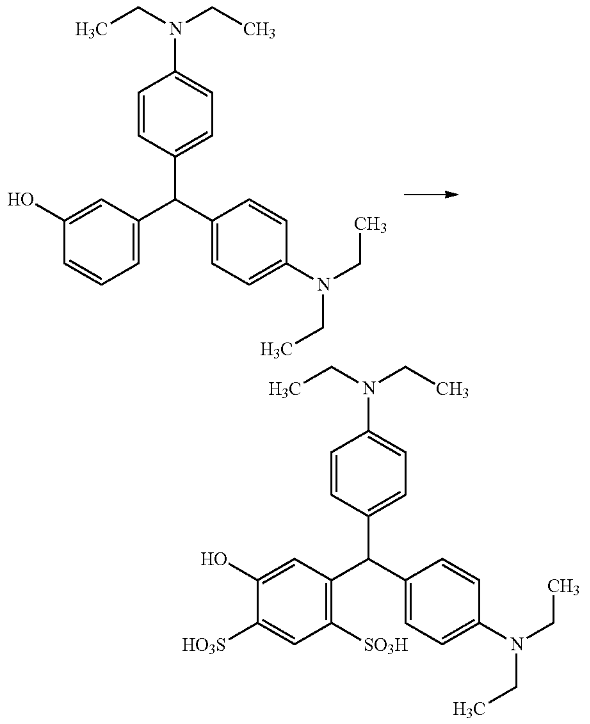

Add 3-(bis(4-(diethylamino)phenyl) methyl) phenol dihydrochloride (150 g, 0.315 mol, 1 eq.) to 600 mL H2SO4.

Heat at 90° C. for 3 hours and then leave stirring for 16 hours at room temperature.

Dilute the reaction medium with 15 L of an ethanol/isopropyl ether mixture (75/25) while keeping the temperature below 20° C.

Filter off the precipitate obtained and wash the solid with 2×600 mL of isopropyl ether.

The solid is dried in a ventilated oven (50° C.).

183 g of 4-(bis(4-(diethylamino)phenyl) methyl)-6-hydroxybenzene-1,3-disulfonic acid are obtained in the form of a white solid.

HPLC purity: 98.8%

Yield: quantitative $^{1}$H NMR (300 MHz, DMSO): 0 10.91 (2H, br s), 8.08 (1H, s), 7.52 (4H, dd, J=8.5 Hz), 7.38 (4H, dd, J=8.6 Hz), 6.95 (1H, s), 6.54 (1H, s), 4.75 (1H, br s), 3.54 (8H, q, J=7.1 Hz), 0.92 (12H, t, J=6.7 Hz)

$^{13}$C NMR (75 MHz, DMSO): δ 153.6, 145.2, 143.0, 137.1, 135.5, 130.8, 128.0, 126.7, 122.3, 118.4, 52.5, 49.2, 10.1

Step 3: Preparation of Patent Blue

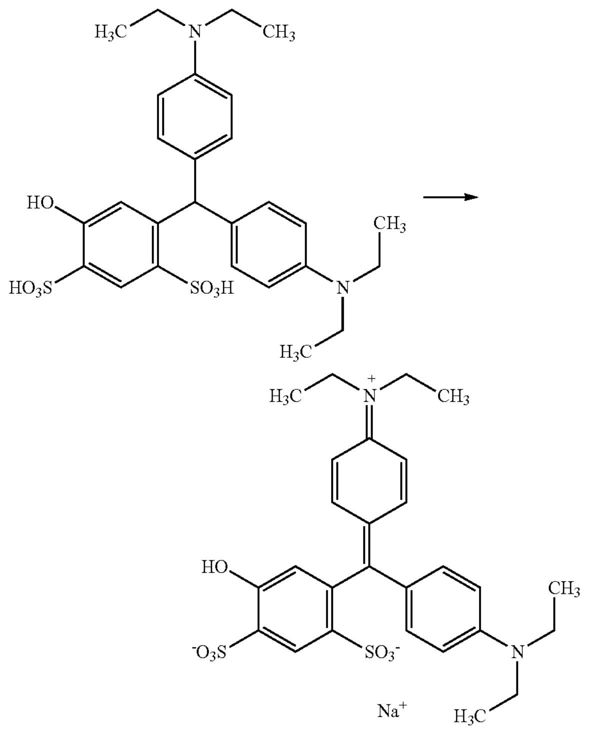

Add 4-(bis(4-(diethylamino)phenyl)methyl)-6-hydroxy-benzene-1,3-disulfonic acid (1.2 kg, 2.1 mol, 1 eq.) to 6 L of N-methylpyrrolidone.

Heat the reaction medium to 95° C. and pour in 1,4-benzoquinone (346 g, 3.2 mol, 1.5 eq.) dissolved in 1.2 L of N-methylpyrrolidone.

Continue heating for 3 hours and then cool to room temperature.

Dilute the reaction medium with 18 L of acetone.

Filter off the precipitate obtained and wash the solid with 2x6 L of acetone.

Take up the solid in 6 L of an H2O/methanol mixture (80/20).

Reflux for 1 hour and then cool to room temperature.

Filter off the solid and wash with 2x6 L of acetone. Take up the solid in 15 L of methanol with stirring and pour into aqueous 22% sodium carbonate solution (256 mL).

Leave stirring for 3 hours and then concentrate.

Take up in 10 L of isopropanol.

Recover the solid by filtration and wash with 2x4 L of acetone.

The solid is dried in a ventilated oven (50° C.).

766 g of 4-[[4-(diethylamino)phenyl]-(4-diethylazanium-ylidenecyclohexa-2,5-dien-1-ylidene)methyl]-6-hydroxy-benzene-1,3-disulfonate sodium salt (patent blue) are obtained in the form of a purple solid.

HPLC purity: 99.3%

Yield: 61%

$^{1}$H NMR (300 MHz, D2O): δ 8.29 (1H, s), 7.24 (4H, dd, J=8.8 Hz), 6.72 (4H, dd, J=8.9 Hz), 6.41 (1H, s), 3.49 (8H, q, J=5.8 Hz), 1.12 (12H, t, J=5.9 Hz)

$^{13}$C NMR (75 MHz, D2O): δ 170.1, 156.6, 154.9, 141.6, 139.7, 133.2, 128.9, 128.2, 125.6, 121.2, 113.5, 45.8, 12.2

Variant of Step 3:

For step 3, the protocol described above was followed, the oxidizing compound being varied. This oxidizing compound could be another quinone or another oxidizing reagent.

The results obtained are collated in Tables 2 and 3 below.

TABLE 2

| Quinone (according to the invention) | Degree of conversion step 3 (*) | Mono-de-ethylated compound % (*) |
|---|---|---|
| 1,4-Benzoquinone | 93% | <1% |
| 3,5-Di-tert-butyl-1,2-benzoquinone | 93% | 2.6% |
| 2,5-Dimethyl-1,4-benzoquinone | 70% | 1.7% |
| 2-Methyl-1,4-benzoquinone | 52% | 2.1% |
| 2,3-Dichloro-5,6-dicyano-1,4-benzoquinone | 31% | 2.4% |
| Tetrachloro-1,4-benzoquinone | 90% | 6.8% |
| Tetrachloro-1,2-benzoquinone | 65% | 4% |
| 2-Chloro-1,4-benzoquinone | 92% | 3.7% |

(*) measured according to the HPLC method described above

It is found that some quinones afford access to high degrees of conversion while leading to a product having little mono-de-ethylated impurity.

TABLE 3

| Oxidizing agent (comparative) | Degree of conversion step 3 (*) | Mono-de-ethylated compound % (*) |
|---|---|---|
| $KMNO_4$ | 95% | 5% |
| $NaMnO_4$ | 78% | 7% |
| Ammonium cerium (IV) nitrate | 41% | 4% |
| $MnO_2$ | 38% | 5% |
| $FeCl_3$ | — | — |

(*) measured according to the HPLC method described above

It is seen that only a few oxidizing reagents other than quinones make it possible to convert compound (V) into patent blue. Few of them are able to afford a de-ethyl content of less than 5%, or with a low degree of conversion. In addition, these reagents are based on heavy metals, the use of which is not recommended, both for ecological reasons and if it is desired to avoid contamination of the final product.

X-ray Powder Diffractogram:

The X-ray powder diffraction profile (diffraction angles) of the patent blue sodium salt obtained in Example 3 is given by the significant lines reported in Table 4 with their intensity and their relative intensity (expressed as a percentage relative to the most intense line).

The measurement was performed on three different batches which all have substantially the same profile as shown in FIG. 1. The batches Inv 1, Inv 2 and Inv 3 were prepared on a pilot scale (3 to 6 kg prepared). This measurement confirms that the crystalline characteristics of the product are constant on conclusion of the preparation process. It also confirms the absence of NaCl (see the characteristic peaks in FIG. 2).

TABLE 4

| 2 theta angle (°) | Interplanar spacing d (Å) | I (counts) | I rel (%) |
|---|---|---|---|
| 5.6 | 15.80 | 500 | 61.5 |
| 6.2 | 14.29 | 375 | 46.2 |
| 9.4 | 9.39 | 187.5 | 23.1 |
| 10.9 | 8.12 | 62.5 | 7.7 |
| 11.5 | 7.71 | 125 | 15.4 |
| 12.1 | 7.33 | 156.25 | 19.2 |
| 14.4 | 6.14 | 343.75 | 42.3 |

TABLE 4-continued

| 2 theta angle (°) | Interplanar spacing d (Å) | I (counts) | I rel (%) |
|---|---|---|---|
| 15.6 | 5.68 | 250 | 30.8 |
| 16.5 | 5.38 | 375 | 46.2 |
| 17.6 | 5.02 | 187.5 | 23.1 |
| 18.2 | 4.86 | 375 | 46.2 |
| 19.4 | 4.57 | 812.5 | 100.0 |
| 20.0 | 4.43 | 500 | 61.5 |
| 22.9 | 3.87 | 187.5 | 23.1 |
| 24.7 | 3.60 | 250 | 30.8 |

Comparison with Commercial Patent Blue, Sodium Salt Products:

Commercial products from the following producers (Table 5) were analysed by the same X-ray diffraction method:

TABLE 5

| Commercial patent blue, sodium salt | | |
|---|---|---|
| Producer | Commercial reference | Reference on FIG. 2 |
| Acros | 339330050 | C1 |
| Santa Cruz Biotechnology | SC250653 | C2 |
| TCI | A1242 | C3 |
| Combi Blocks | HA8936 | C4 |
| Biosynth | FC1571 | C5 |
| Colorey | FG18191327 | C6 |

The results are collated in FIG. 2. It is seen that most of the peaks do not correspond to those of the patent blue, sodium salt of the invention which are reported in Table 4 and in FIG. 1. This observation leads to the conclusion that the patent blue, sodium salt of the invention is a new crystalline form relative to the crystalline forms already known. In FIG. 2, the presence of peaks characteristic of NaCl is also observed, notably the peaks at the 2 theta angles=32 and 45.5, which makes it possible to note the presence of NaCl in all the commercial patent blue samples, but not in the patent blue sodium salt according to the invention.

The invention claimed is:

1. A process for synthesizing a compound corresponding to formula (I), the process comprising:

(a) condensing a benzaldehyde compound of formula (II) with dialkylaniline of formula (III) to give a triphenylmethane of formula (IV)

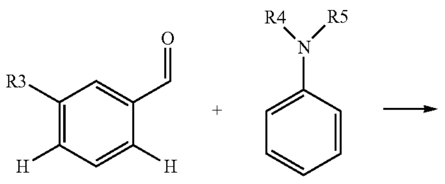

(II) (III)

-continued

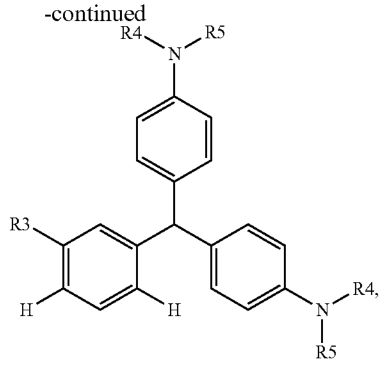

(IV)

R3, R4, and R5 being as defined for formula (I);

(b) treating the triphenylmethane of formula (IV) with sulfuric acid to form a triphenylmethane sulfone of formula (V)

(V)

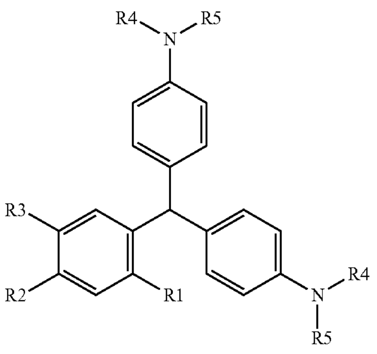

R1, R2, R3, R4, and R5 being as defined for formula (I); and (c) oxidizing the triphenylmethane sulfone of the formula (V) with a quinone to obtain the compound of formula (I)

(I)

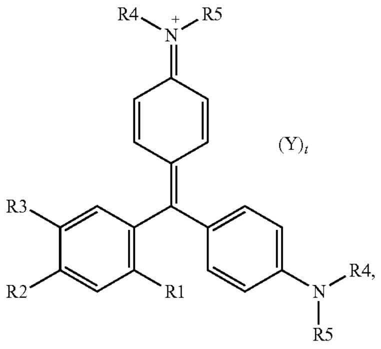

wherein

R1 and R2 are independently —$SO_3H$ or —$SO_3^-$,

R3 is —OH, —OR', or —OCOOR', where R' is a $C_1$-$C_8$ alkyl, a $C_2$-$C_8$ alkenyl, a phenyl, or a benzyl, R4 and R5 are independently a $C_1$-$C_8$ alkyl, a $C_2$-$C_8$ alkenyl, a phenyl, or a benzyl, wherein two groups R4 and R5 borne by the same nitrogen atom optionally together form a ring including the nitrogen atom, Y is an organic or inorganic cation which is pharmaceutically acceptable salt, and t is 0, ½, or 1.

2. The process of claim 1, further comprising, after the oxidizing (c), a salification (d).

3. The process of claim 1, wherein the compound of formula (I) has formula (IA)

(IA)

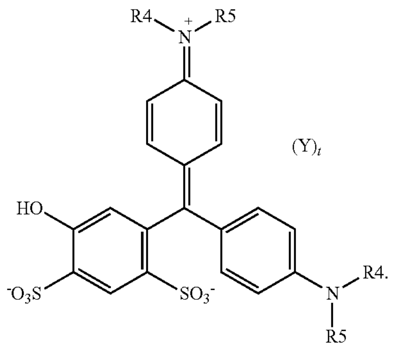

4. The process of claim 3, wherein the compound of formula (IA) has formula (VI) or (VII):

(VI)

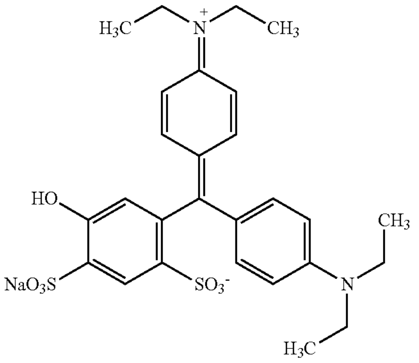

or (VII)

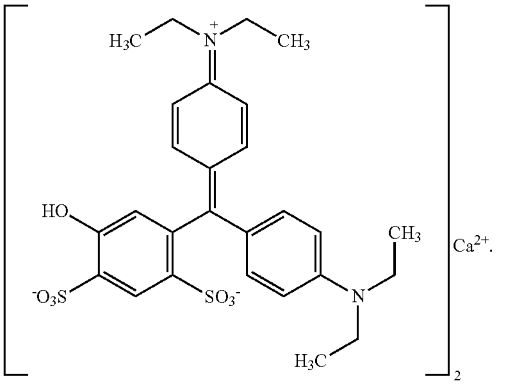

5. The process of claim 1, in which, in the treating b), the reaction medium is maintained at a temperature ranging from 70° C. to 120° C. for a period ranging from 1 to 5 hours.

6. The process of claim 1, further comprising, on conclusion of the treating (b), precipitating out the triphenylmethane sulfone of formula (V).

7. The process of claim 1, wherein, in the oxidizing (c), the quinone comprises 1,4-benzoquinone, 1,2-benzoquinone, a di($C_1$-$C_4$)alkyl-1,4-benzoquinone, a di($C_1$-$C_4$)alkyl-1,2-benzoquinone, a mono($C_1$-$C_4$)alkyl-1,4-benzoquinone, or a mono($C_1$-$C_4$)alkyl-1,2-benzoquinone.

8. The process of claim 1, wherein the oxidizing (c) is performed in an apolar protic solvent, at a temperature in a range of from 40 to 120° C.

9. The process of claim 1, which produces a composition comprising at least 99.0% of the compound of formula (I), the percentage being measured by high-performance liquid chromatography with detection at 230 nm.

10. The process of claim 3, which produces a composition comprising at least 99.0% of the compound of formula (IA), the percentage being measured by high-performance liquid chromatography with detection at 230 nm.

11. The process of claim 1, which provides a crystalline form of the compound of formula (VI)

(V)

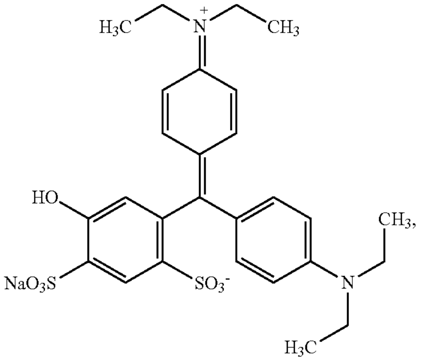

wherein the crystalline form has an X-ray powder diffraction diagram, measured on a diffractometer and expressed in terms of interplanar spacing d, 2 theta Bragg angle, intensity, and relative intensity, expressed as a percentage relative to the most intense line:

| 2 theta angle (°) | Interplanar spacing d (Å) | I (counts) | I rel (%) |
|---|---|---|---|
| 5.6 | 15.80 | 500 | 61.5, |
| 6.2 | 14.29 | 375 | 46.2, |
| 9.4 | 9.39 | 187.5 | 23.1, |
| 10.9 | 8.12 | 62.5 | 7.7, |
| 11.5 | 7.71 | 125 | 15.4, |
| 12.1 | 7.33 | 156.25 | 19.2, |
| 14.4 | 6.14 | 343.75 | 42.3, |
| 15.6 | 5.68 | 250 | 30.8, |
| 16.5 | 5.38 | 375 | 46.2, |
| 17.6 | 5.02 | 187.5 | 23.1, |
| 18.2 | 4.86 | 375 | 46.2, |
| 19.4 | 4.57 | 812.5 | 100.0, |
| 20.0 | 4.43 | 500 | 61.5, |
| 22.9 | 3.87 | 187.5 | 23.1, and |
| 24.7 | 3.60 | 250 | 30.8, |

wherein values of the intensity (I) and the relative intensity (I rel) can vary by ±15%.

12. A process for manufacturing a medicament or a diagnostic product, the process comprising:

making the compound of formula (I) by the process of claim 1; and introducing the compound of formula (I) into a pharmaceutically acceptable support.

13. The process of claim 12, wherein the compound of formula (I) is patent blue.

14. The process of claim 13, wherein the compound of formula (I) is a crystalline form of the patent blue, sodium salt, corresponding to formula (VI), (VI)

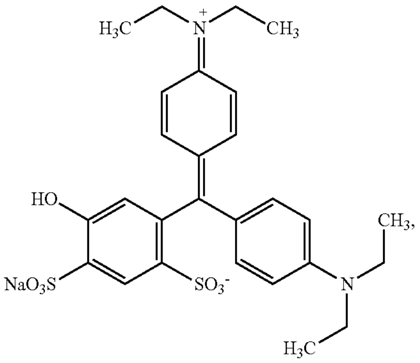

wherein the crystalline form has an X-ray powder diffraction diagram, measured on a diffractometer and expressed in terms of interplanar spacings d, 2 theta Bragg angle, intensity, and relative intensity, expressed as a percentage relative to the most intense line:

| 2 theta angle (°) | Interplanar spacing d (Å) | I (counts) | I rel (%) |
|---|---|---|---|
| 5.6 | 15.80 | 500 | 61.5, |
| 6.2 | 14.29 | 375 | 46.2, |
| 9.4 | 9.39 | 187.5 | 23.1, |
| 10.9 | 8.12 | 62.5 | 7.7, |
| 11.5 | 7.71 | 125 | 15.4, |
| 12.1 | 7.33 | 156.25 | 19.2, |
| 14.4 | 6.14 | 343.75 | 42.3, |
| 15.6 | 5.68 | 250 | 30.8, |
| 16.5 | 5.38 | 375 | 46.2, |
| 17.6 | 5.02 | 187.5 | 23.1, |
| 18.2 | 4.86 | 375 | 46.2, |
| 19.4 | 4.57 | 812.5 | 100.0, |
| 20.0 | 4.43 | 500 | 61.5, |
| 22.9 | 3.87 | 187.5 | 23.1, and |
| 24.7 | 3.60 | 250 | 30.8, |

wherein values of the intensity (I) and the relative intensity (I rel) can vary by +15%.

15. The process of claim 1, wherein, in the oxidizing (c), the quinone comprises 1,4-benzoquinone.

* * * * *